(12) United States Patent
Howard et al.

(10) Patent No.: US 8,445,705 B2
(45) Date of Patent: May 21, 2013

(54) PRODUCTION OF 5-MEMBERED AND 6-MEMBERED CYCLIC ESTERS OF POLYOLS

(75) Inventors: Stephen Howard, Sherman, IL (US); Alexandra Sanborn, Lincoln, IL (US)

(73) Assignee: Archer Daniels Midland Company, Decatur, IL (US)

( * ) Notice: Subject to any disclaimer, the term of this patent is extended or adjusted under 35 U.S.C. 154(b) by 101 days.

(21) Appl. No.: 12/993,143

(22) PCT Filed: May 28, 2009

(86) PCT No.: PCT/US2009/045383
§ 371 (c)(1),
(2), (4) Date: Nov. 17, 2010

(87) PCT Pub. No.: WO2009/155020
PCT Pub. Date: Dec. 23, 2009

(65) Prior Publication Data
US 2011/0071305 A1    Mar. 24, 2011

Related U.S. Application Data

(60) Provisional application No. 61/056,678, filed on May 28, 2008.

(51) Int. Cl.
*C07D 493/04*    (2006.01)

(52) U.S. Cl.
USPC ............................................... 549/464

(58) Field of Classification Search
USPC ........................................................ 549/464
See application file for complete search history.

(56) References Cited

U.S. PATENT DOCUMENTS

| 3,951,945 | A  | 4/1976  | Heesen et al. |
| 7,220,710 | B2 | 5/2007  | Kunz et al. |
| 2005/0027135 | A1 | 2/2005 | Ramprasad et al. |
| 2007/0173421 | A1 | 7/2007 | Nakanishi et al. |
| 2007/0282042 | A1 | 12/2007 | East |

OTHER PUBLICATIONS

Duxbury et at,. Observations on Esterification Reachons, Carbohydrate Research, 2((1966), pp. 122-131.
Kurszewska et al., The solvent-free thermal dehydration of hexitols on zeolites. Carbohydrate Research, 337 (2002), pp. 1261-1268.

*Primary Examiner* — Taofiq A Solola
(74) *Attorney, Agent, or Firm* — Mark W. Roberts

(57) ABSTRACT

Described herein are improved methods for the preparation of 5- and 6-membered cyclic mono and diesters of sugar alcohols and anhydrosugar alcohols by reaction with an organic acid RCOOH over a solid acidic substrate. The process is adaptable to a continuous process for simultaneously making and separating the cyclic esters from the sugar alcohols and anhydrosugar alcohols under mild conditions using the solid acid substrate as both the catalyst and a chromatographic bed for separation. The reactions are performed at mild temperatures of 70° C. to 100° C. and the formation of the cyclic esters is nearly quantitative. Also described is a method for making 5- and 6-membered cyclic mono and diesters of sugar alcohols and anhydrosugar alcohols using microwave irradiation in the presence of the organic acid.

25 Claims, 4 Drawing Sheets

PRODUCTION OF 5-MEMBERED AND 6-MEMBERED CYCLIC ESTERS OF POLYOLS

PRIORITY CLAIM

This application is a 35 U.S.C. §371 national phase entry of International Application No. PCT/US2009/045383 filed May 28, 2009, which claims priority to U.S. provisional patent application No. 61/056,678 filed May 28, 2008, which is incorporated herein by reference in its entirety.

FIELD OF INVENTION

This application pertains to an improved method for the preparation of 5- and 6-membered cyclic esters of 5 and 6 carbon polyols. In particular, the application relates to a continuous process for making and separation of cyclic esters from sugar alcohols and anhydrosugar alcohols under mild conditions using a solid acid substrate as a catalyst.

BACKGROUND

Cyclic esters of sugar alcohols such as D-sorbitol and D-mannitol have wide commercial utility as a lubricant or hydraulic oil as well as non-ionic emulsifying agents, power train and heat transfer media, dielectrics, process oils and solvents. These cyclic esters are environmentally friendly, biodegradable oils and lubricants. Simple and cost effective methods of producing five- and six-membered cyclic esters from sugar alcohols and their dehydration products are desired.

SUMMARY

The present teaching provides a simple and cost effective method for the preparation and separation of 5- and 6-membered cyclic esters of sugar alcohols and their monoanhydro and dianhydro derivatives by reaction with an organic acid on a solid acid catalyst bed, which is adaptable for use in a continuous flow process for simultaneous synthesis and separation of the esters from the starting sugar alcohols or their monoanhydro and dianhydro derivatives.

DETAILED DESCRIPTION

Figure 1:
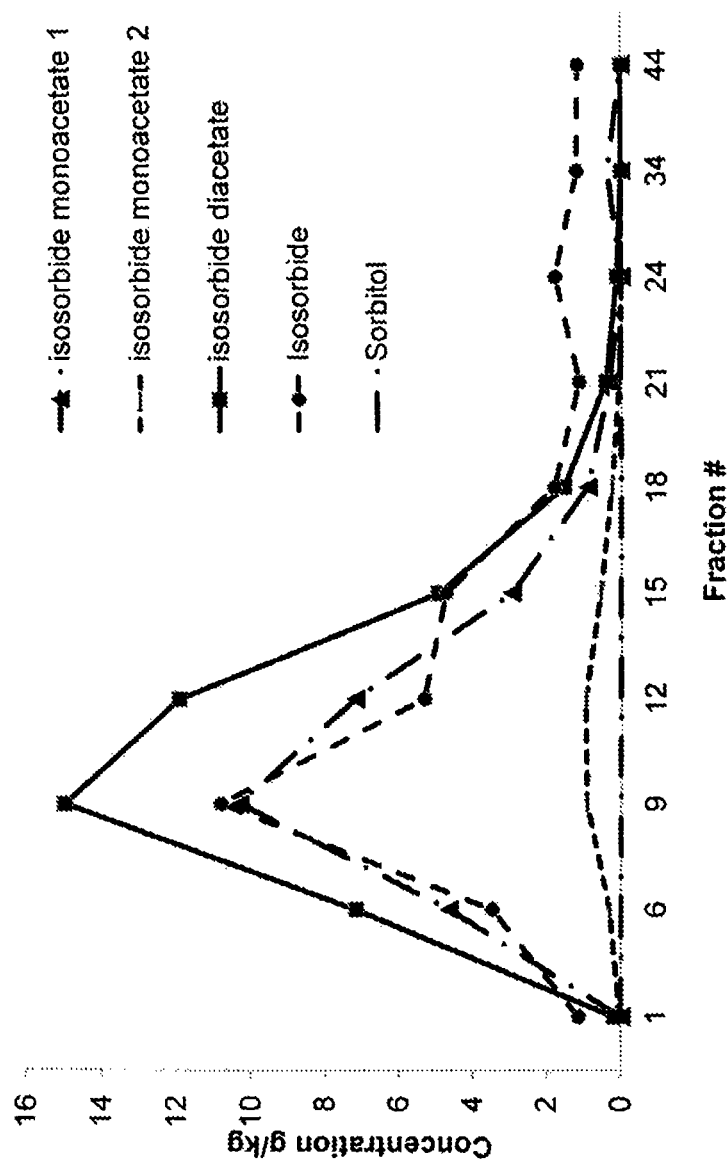
FIG. 1 shows a chromatographic profile for simultaneous synthesis of cyclic mono and diesters from sorbitol and acetic acid and chromatographic separation from sorbitol on an acidic resin that acts as a catalyst and chromatographic separation media.

This disclosure relates to a chromatographic process to synthesize cyclic esters of 5 and 6 carbon sugar alcohols and their monanhdydro and dianhydro derivatives in accordance with the following reaction scheme:

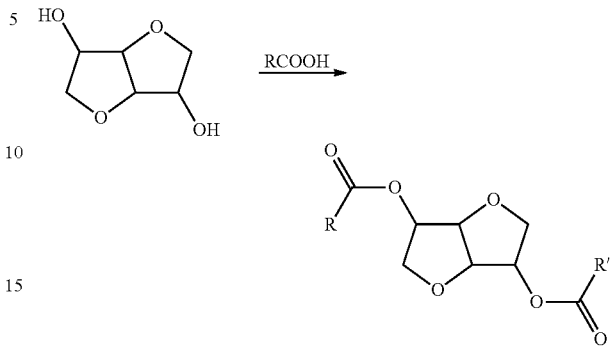

where R and R' are independently hydrogen, alkyl, aryl, vinyl, alkenylallyl. Isosorbide, which is the starting material depicted above is an end product of the progresseive acid catalyzed dehydration of sorbitol to first the monoanhdyo then the dianhydro sugar alcohol according to the reaction scheme below:

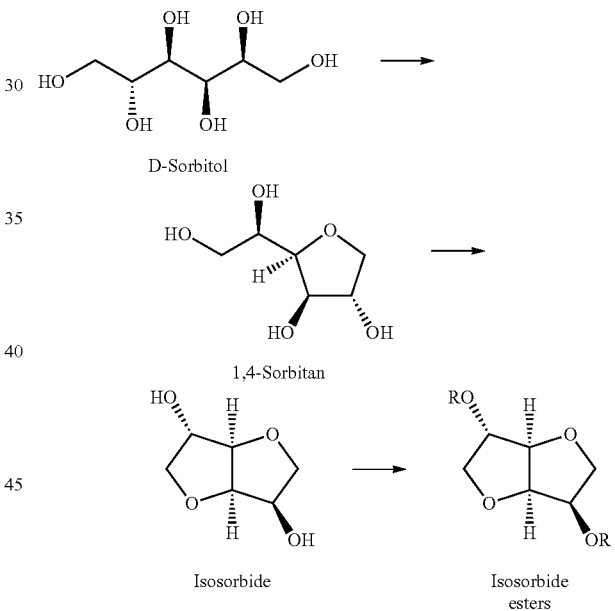

Because acid catalyzes the dehydration as well as the ultimate esterification with the added organic acid, the starting materials useful in the present teaching can be any polyol that undergoes acid catalyzed dehydration. Typical polyol starting materials include sugar alcohols, monoanhydrosugar and dianhydrosugar alcohols, dianhydrosugar monoesters or a mixture of such alcohols. Accordingly, the term "polyol" is used generically herein to be inclusive of the aforementioned sub genus of compounds. Generally, the preferred starting materials include arabinitol, ribitol, sorbitol, mannitol, isosorbide, sorbitan, isoiodide, isomannide, galactitol and iditol. Pentitols such as xylitol can also be used. Isosorbide, which is the dianhydro sugar alcohol derivative of sorbitol, is depicted in the reaction above and is a particularly preferred starting material because it is readily available or easily made from the dehydration of sorbitol. Sorbitan which is the monanhydro sugar alcohol derivative of sorbitol is also a desirable starting material, but the reaction works with sorbitol and other polyols as well. The starting materials may be "crude", i.e., contained in an impure state as mixtures with one another or with minor non-reactive impurities.

In a typical practice, the reaction is carried out on a solid acid catalyst. Examples of such solid acids include acidic resins such as Amberlyst 35, Amberlyst 15, Amberlyst 36, Amberlyst 70, and Amberlyst 131 from Rohm and Haas; Purolite CT-145, Lewatit S2328, Lewatit K2431, Lewatit S2568, Lewatit K2629 from Bayer Company; and Dianion SK104, PK228, RCP160 and Relite RAD/F from Mitsubishi Chemical America, Inc. In differing embodiments, the solid acid catalyst may be a weak or a strong acid catalyst. In other practices, the solid acid catalyst can be acid groups associated with non-resin substrates such as clays, zeolites, alumina, etc. Examples of such solid acids include zeolites such as CBV 3024, 5534G, T-2665, T-4480, and CS331-3. The solid acid catalyst may be a calcined zeolite.

One process involves exposure of a mono or dianhydrosugar alcohol or sugar alcohol to an acid catalyst in the presence of an organic acid RCOOH, at a temperature and pressure for a period of time (dependent on reaction conditions) sufficient to provide mono and dianhydrosugar esters, which are mono cyclic or dicyclic respectively. Another independent but related process involves microwave irradiation of the polyol in the presence of the organic acid including but not limited to a sugar alcohol and an anhydrosugar alcohol to provide cyclic esters.

The reactions conditions are preferably relatively mild. The reaction is carried out at a temperature from about 70° C. to about 100° C. at ambient pressure. More typically the reaction temperature is about 80 ° C. to 100° C. and in exemplary practices the reaction temperature is about 85° C. When the acid catalyst is in the form of a column bed, the column can be equilibrated with the desired organic acid (RCOOH) and the reaction commenced by heating the bed to the desired temperature and loading the sugar alcohol or anhydro sugar alcohol to one end of the column. The column may be eluted using the same organic acid as the eluent. The passage of the reactants over the column bed affects a simultaneous synthesis of the polyol esters and chromatographic separation of the esters from unreacted sugar alcohol or anhydrosugar alcohol As shown in FIG. 1, unreacted sorbitol tends to elute after the peak of isosorbide esters. As shown best in FIG. 2, unreacted isorbide tends to elute just before the peak of isosorbide esters Following separation of the product from the reaction mixture, further purification of the different esters can be done using procedures such as recrystallization or distillation or other chemical purification techniques well known in the art.

The use of a column(s) in the synthetic and purification processes enables a continuous flow of a heated anhydrosugar alcohol or sugar alcohol solution, thereby decreasing the amount of by-product formation, polymerization, and resin deactivation. The use of solid phase catalysts to chromatographically synthesize and separate isosorbide esters and cyclic esters of polyols is novel.

When the starting source is a sugar alcohol material, the intermediate compounds of monoanhydrosugar alcohol and dianhydrosugar alcohol may be obtained and recycled to give the desired ester products. Another unique aspect of this teaching is that any fraction containing unreacted sugar alcohol or anhydrosugar alcohol can be allowed to react again by recycling onto the column. Mixed fractions can be rechromatographed. This process differs from prior art in that sorbitol containing fractions may be recycled until pure isosorbide esters are obtained. As opposed to the process of the present teaching, recycling of starting material heretofore has not been an option and longer reaction times have led to polymerization and tar formation. In the present teaching, the recycling of sugar alcohol and anhydrosugar alcohol containing mixtures (fractions) through a solid phase catalyst to generate and separate cyclic esters of polyols and anhydro derivatives thereof does not produce the polymerization and tar formation as in the prior art.

The experimental design and set up of this process is not limited. Multiple chromatographic columns may be used when the feeding amount for the chromatography is especially high. This aspect of this disclosure is advantageous for industrial scale development. The material may flow through all of the resin columns or an elution stream may be inserted such that only a remainder of the stream passes through the complete system. For example, several columns may be used specifically for synthesis and a few columns used for separation and purification. Alternatively, the system may be but not limited to a jacketed glass column, a falling film evaporator, a simulated moving bed, continuous setup (CSEP), or a continuous flow pipe system.

Figure 4:
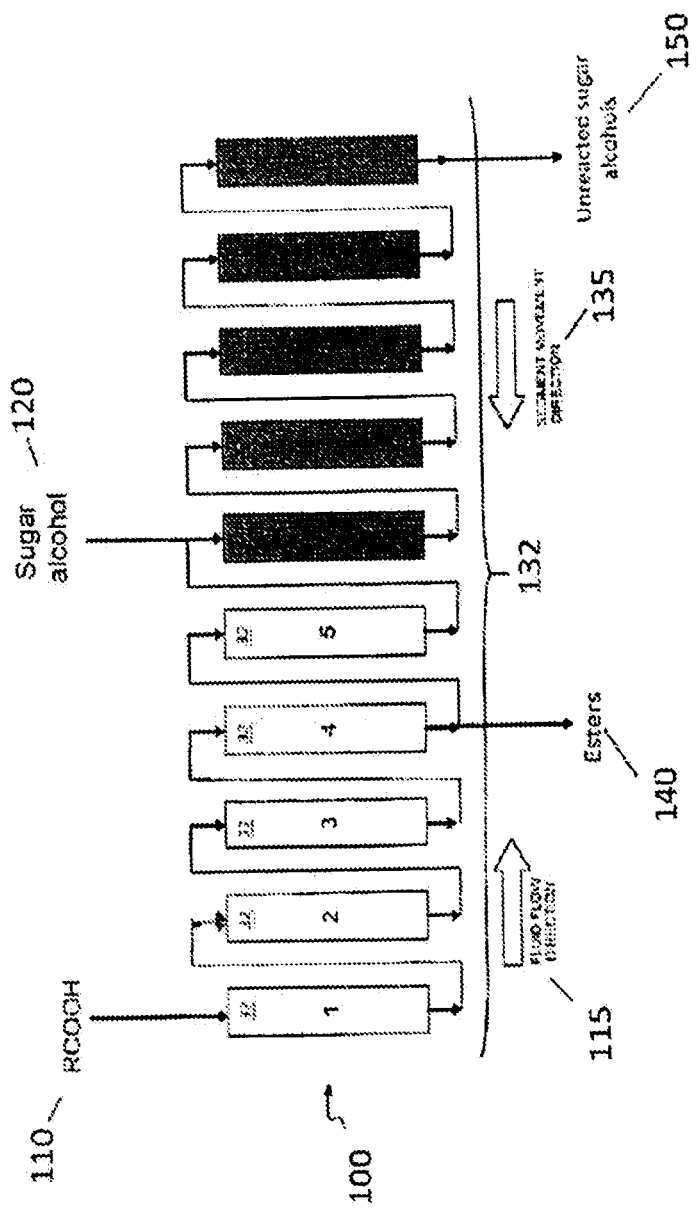
FIG. 4 schematically depicts a continuous simulated moving bed chromatographic process for the preparation of cyclic esters from sugar alcohols or their monoanhydro or dianhydro derivatives.

A continuous chromatographic separation process using a simulating moving bed chromatographic device such as a CSEP system 100 is schematically illustrated in FIG. 4. The CSEP system 100 includes a continuous stationary phase column bed 132 separated into a plurality (1-10) of segmented beds 32 on a carousel 132. The liquid moving phase, is loaded from one end of a first bed segment 32(1) and is passed from the opposite end of the first bed segment 32(1) to the top of the next adjacent bed segment in the carousel 13(2) in fluid flow direction 115. At the same time the plurality of column bed segments 32 are rotated in carousel 132 in bed movement direction 135 that is counter current to the fluid direction 115. Reactants are fed into segments of the column at a first zone (depicted at segment 32(1)) for organic acids 110 and at second zone (depicted at segment 32(6) for sugar alcohols 120, each in the fluid flow direction 115. It is understood in this depiction that sugar alcohols 120 may include or be replaced by mono and/or anhydro derivatives thereof. The sugar alcohols 120 and organic acids 110 contact each other over the catalytic bed 132 maximally in reaction zones of the carousel bed depicted as column segments 32(6) through 32(9). The ester products 140 preferentially partition with the stationary phase of the column beds 32 relative to the sugar alcohols 120, therefore, as the bed segments are rotated in bed flow direction 135 the ester products 140 preferentially move with the bed segments and are eluted in a product elution zone depicted as segment 32(4). In contrast, the sugar alcohols 120 relative to the esters 140 preferentially partition with the liquid phase of organic acid 110 and therefore flow toward an opposing portion of bed 132 and can be withdrawn from an elution zone that is enriched with unreacted sugar alcohols 150 depicted at segment 32(10) of column bed 132. In an optional embodiment, the eluted sugar alcohols 150 can be combined with the input sugar alcohols 120 to maximize reactant utilization. Optionally, a wash elution zone may be introduced between the elution zone at column segment 32(1) and the reload zone at column segment 32(1) to regenerate the column bed, in which case an additional wash elution port would be configured to collect the waste product In any case, when hen the overall fluid flow between input organic acid 110 and sugar alcohols is properly balanced with the removal of product esters 140 and unreacted sugar alcohols 150 product and elution the effect is to establish continuous formation of product and continuous chromatographic separation that can be conducted indefinitely, subject only to the life of the column bed.

The process of described herein may also be applied to crude isosorbide reaction mixtures containing unreacted sorbitol. Also, the present teaching does not involve the use of toxic chemicals, and does not require expensive enzymes. Also, a variety of isosorbide esters can be prepared using this process by modifying the choice of organic acid solvent. For example, a continuous flow of an acetic acid solution of sorbitol, sorbitan, isosorbide, or a mixture thereof through a solid phase catalyst can result in the formation of mono- and/or di-acetylated isosorbide. While exemplified herein with acetic acid, the organic acids useful for forming cyclic esters may be any branched or straight chain alkanoic acids, substituted and unsubstituted aryl carboxylic acids, alkenoic acids, dicarboxylic acids, fatty acids or mixtures thereof. Typical organic acids of interest include formic acid, acetic, propionic, and butyric acid. Also useful are compound with multiple acid groups such as diacids like succinic acid, tartaric acid, or fumaric acid and tri-acids like citric acid.

In addition to the above in an entirely different embodiment it has been discovered that, exposure of anhydrosugar alcohols to microwave radiation in the presence of an organic acid and an inorganic acid catalyst in the liquid phase also provides a method for forming cyclic esters from sugar alcohols and anhydro derivatives thereof. Optionally an organic solvent that is inert to the reaction conditions may be included. In an exemplary embodiment, dioxane is used.

Additional solvents may include but are not limited to; methyltetrahydrofuran, cyclopentylmethyl ether, alkylated polyether solvents, ketones solvents such as methyl ethyl ketone, methyl isobutyl ketone and amide solvents such as dimethyformamide (DMF), dimethylacetamide (DMAC) and N-methyl pyrrolidinone (NMP).

The inorganic acid catalyst can be for example, hydrochloric acid, sulfuric acid, phosphoric acid, or hydrofluoric acid. While oxygenated acids such as sulfuric acid, phosphoric acid are useful for catalyzing the reaction they may also form cyclic sulfoesters or phosphoesters of the sugar alcohol or anhydro derivative thereof as unwanted byproducts. Microwave assisted synthesis of isosorbide esters allows for the enhancement of reaction rates, ease of manipulation, and precise control over reaction conditions (see Example 3 below). The reaction temperature for microwave assisted synthesis of the cyclic esters is typically between 120° C. and 200° C., more typically between 140° C. and 180° C., and in an exemplary embodiments is about 160° C. These temperatures are higher than required for synthesis using a solid phase acid catalyst and the process does not result in a separation of the unreacted products from the diesters. However, the microwave facilitated reaction is less costly, faster, and easier to execute. Sugar alcohols, crude mixtures of sugar alcohols, crude mixtures of anhydrosugar alcohols, including monoanhydrosugar and dianhydro derivatives thereof or mixtures thereof may also be used as a starting source. The process may be performed in batch or continuously using a pipe, tubing, or similarly constructed flow-through reactor system.

The following examples illustrate specific embodiments of the present teaching, but is not to be considered as limiting the invention in any manner.

Example 1

Preparation of Isosorbide Diacetate from Sorbitol

Amberlyst 35 resin (50 g) soaked in acetic acid is added to a column heated to 85° C. The temperature of the column was maintained at 85° C. and a solution of sorbitol (5.00 g) in acetic acid (10 mL) was added. The solution was eluted through the column at a flow rate of 1.2 mL/min. The major product was isosorbide diacetate with the monoacetates also present. The products eluted from the column are summarized in Table 1 and depicted in FIG. 1.

TABLE 1

Isosorbide Diacetate Formation using Amberlyst 35 Resin Column from Sorbitol.

| Fraction Number | isosorbide monoacetate g/kg | Isosorbide Monoacetate g/kg | Isosorbide Diacetate g/kg | Isosorbide g/kg | Sorbitol | Acetic Acid g/kg |
| --- | --- | --- | --- | --- | --- | --- |
| 1 | 0.00 | | 0.2 | 1.14 | 0.00 | 963.09 |
| 6 | 4.65 | 0.31 | 7.2 | 3.48 | 0.00 | 923.11 |
| 9 | 10.32 | 0.92 | 15.0 | 10.84 | 0.00 | 861.93 |
| 12 | 7.20 | 0.95 | 11.9 | 5.33 | 0.00 | 911.44 |
| 15 | 2.96 | 0.56 | 5.0 | 4.74 | 0.01 | 953.86 |
| 18 | 0.91 | 0.26 | 1.6 | 1.82 | 0.00 | 947.13 |
| 21 | 0.32 | 0.06 | 0.4 | 1.14 | 0.04 | 975.11 |
| 24 | 0.0 | 0.0 | 0.1 | 1.80 | 0.00 | 977.42 |
| 34 | 0.0 | 0.0 | 0.0 | 1.20 | 0.37 | 982.22 |
| 44 | 0.0 | 0.0 | 0.0 | 1.17 | 0.00 | 975.18 |

Example 2

Preparation of Isosorbide Diacetate from Isosorbide

Figure 2:
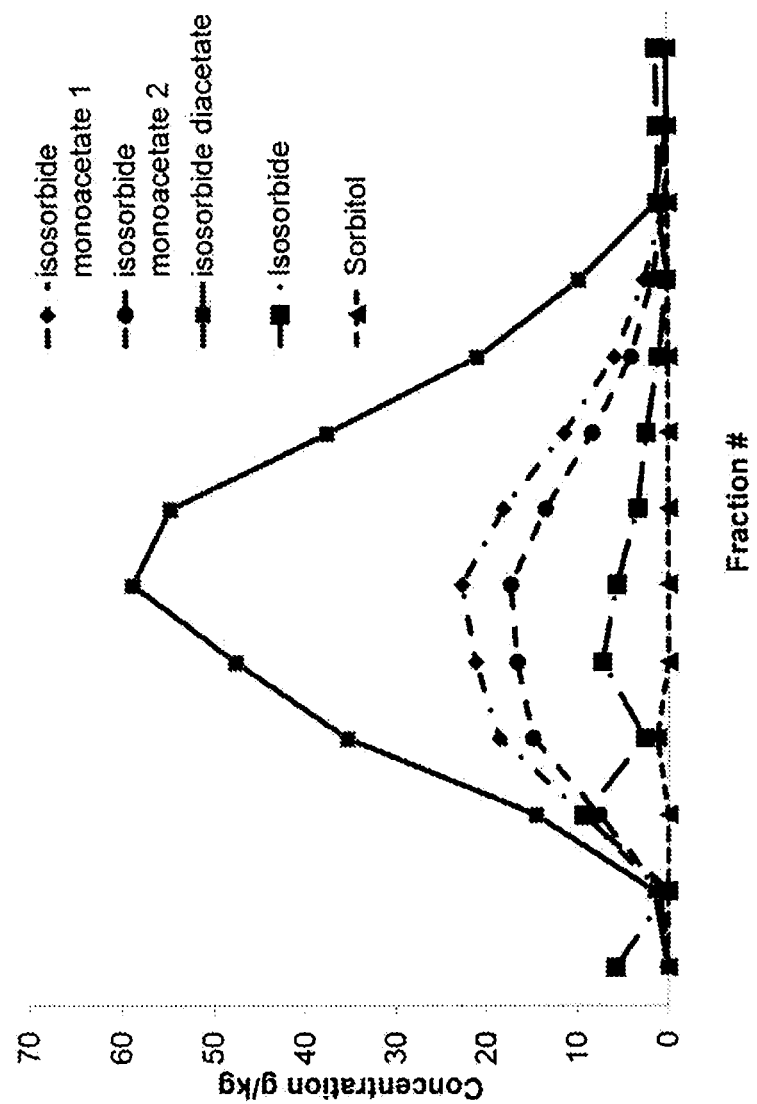
FIG. 2 shows a chromatographic profile for simultaneous synthesis of cyclic mono and diesters from isosorbide and acetic acid and chromatographic separation from isosorbide on an acidic resin acts as a catalyst and chromatographic separation media.

Amberlyst 35 resin (50 g) soaked in acetic acid is added to a column heated to 85° C. The temperature of the column was maintained at 85° C. and a solution of isosorbide (5.01 g) in acetic acid (10 mL) was added. The solution was eluted through the column at a flow rate of 1.2 mL/min. The major product was isosorbide diacetate with the monoacetates also present. Table 2 below summarizes the products eluded from the column which are also depicted in FIG. 2.

TABLE 2

Column Elution of Isosorbide through Amberlyst 35 resin packed in Acetic Acid

| Fraction Number | isosorbide monoacetate 1 g/kg | Isosorbide monoacetate 2 g/kg | isosorbide diacetate g/kg | Isosorbide g/kg | Sorbitol g/kg | Acetic Acid g/kg |
|---|---|---|---|---|---|---|
| 1 | 0.07 | 0.00 | 0.1 | 5.76 | 0.00 | 964.95 |
| 9 | 0.93 | 0.80 | 1.5 | 0.00 | 0.00 | 965.53 |
| 12 | 9.37 | 7.62 | 14.6 | 9.32 | 0.00 | 936.88 |
| 15 | 18.64 | 14.90 | 35.4 | 2.57 | 1.22 | 890.82 |
| 18 | 21.26 | 16.65 | 47.7 | 7.25 | 0.00 | 867.42 |
| 21 | 22.76 | 17.37 | 58.9 | 5.66 | 0.00 | 840.81 |
| 24 | 18.16 | 13.49 | 54.8 | 3.34 | 0.00 | 856.06 |
| 27 | 11.40 | 8.31 | 37.7 | 2.39 | 0.00 | 896.16 |
| 30 | 5.88 | 4.04 | 21.0 | 1.04 | 0.00 | 939.99 |
| 33 | 2.55 | 1.71 | 9.8 | 0.15 | 0.12 | 961.69 |
| 40 | 0.44 | 0.29 | 1.4 | 1.02 | 0.00 | 968.60 |
| 46 | 0.12 | 0.06 | 0.1 | 1.11 | 0.00 | 972.50 |
| 54 | 0.07 | 0.00 | 0.1 | 1.25 | 0.00 | 991.09 |

Example 3

Microwave Assisted Synthesis of Isosorbide Diacetate from Isosorbide

Figure 3:
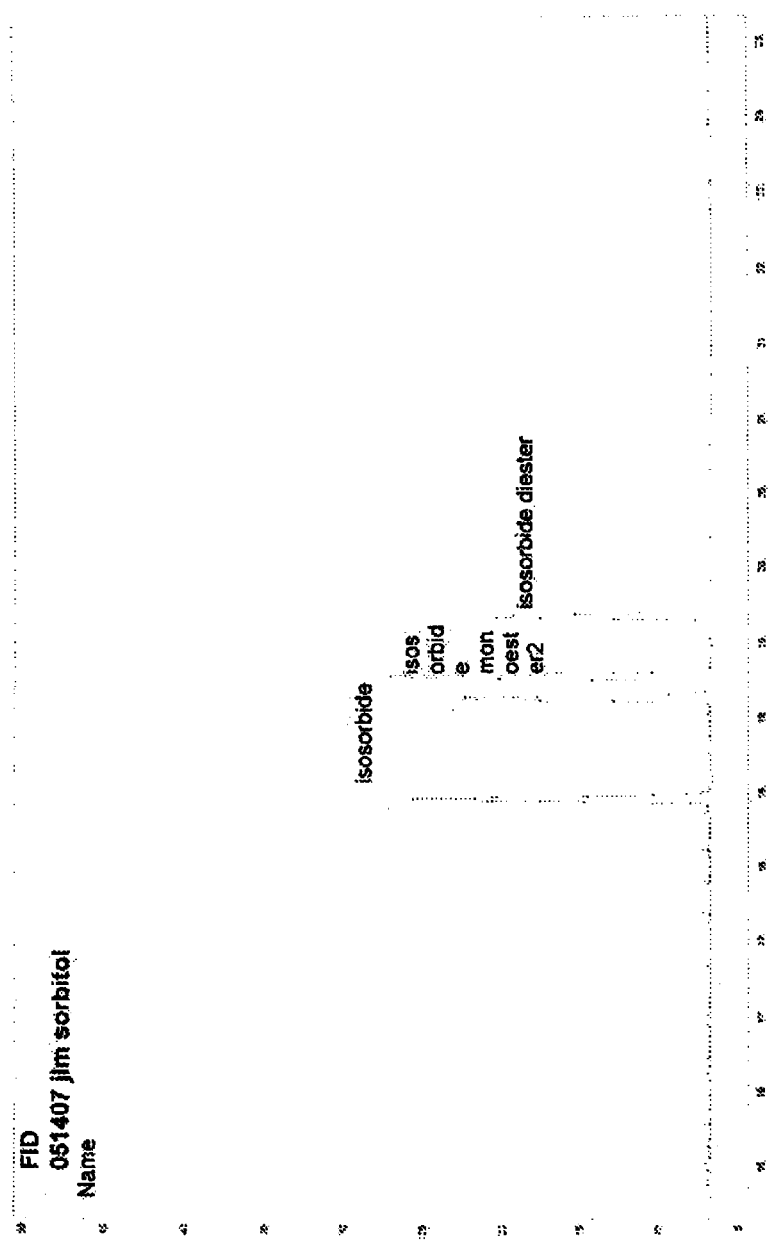
FIG. 3 shows an HPLC analysis to identify mono and diesters made by microwave facilitated reaction of acetic acid and isosorbide.

A sample of isosorbide (3 g), acetic acid (30 mL), and 4M HCl in dioxane (1 mL) were placed in a Teflon-lined reaction vessel inside a high density rotor for treatment in a MicroSYNTH Microwave Labstation. The sample was heated from room temperature to 160° C. in 2 min, and kept at 160° C. for 20 min using an irradiation power of 1000 Watt. The vessel was cooled. The final product was composed of 18.9% isosorbide, 14.7% monoester 1, 18.8% monoester 2, and 12.5% diester, which are illustrated in HPLC chromatogram depicted in FIG. 3.

The yields disclosed herein are exemplary only and do not necessarily reflect the optimal yields possible when reaction conditions are optimized.

While this invention has been described with reference to several preferred embodiments, it is contemplated that various alterations and modifications thereof will become apparent to those skilled in the art upon a reading of the preceding detailed description. It is therefore intended that the following appended claims be interpreted as including all such alterations and modifications as fall within the true spirit and scope of this invention.

What is claimed is:

1. A method of preparing cyclic esters from 5 or 6 carbon compounds comprising, contacting a column bed containing a solid acid catalyst with at least one starting 5 or 6 carbon compound selected from the group consisting of a sugar alcohol, a monoanhydrosugar alcohol, and a dianhydrosugar alcohol in the presence of an organic acid at a temperature from 80° to 100° C. for a time sufficient to form at least one of a cyclic monoester and cyclic diester derivative of at least one of the monoanhydrosugar alcohol and a dianhydrosugar alcohol, and eluting at least one of the cyclic monoester and diester derivative from the column bed separately from the starting 5 or 6 carbon compound.

2. The method of claim 1 wherein eluting the column bed comprises a chromatographic separation of the 5 or 6 carbon starting compound from at least one of the cyclic monoester and cyclic diester derivative.

3. The method of claim 2 wherein the bed is configured in a simulated moving bed apparatus and the contacting and chromatographic separation are performed continuously.

4. The method of claim 1, wherein the organic acid is acetic acid.

5. The method of claim 1 wherein the starting 5 or 6 carbon compound is selected from group consisting of sorbitol, isosorbide and sorbitan.

6. The method of claim 1 wherein the starting 5 or 6 carbon compound is selected from the group consisting of arabinitol, ribitol, sorbitol, mannitol, isomannide, galactitol, iditol and xylitol.

7. The method of claim 3, wherein the starting 5 or 6 carbon compound is sorbitol.

8. The method of claim 3, wherein the starting 5 or 6 carbon compound is isosorbide.

9. The method of claim 1 wherein the solid acid catalyst is an ion exchange resin.

10. The method of claim 9 wherein the solid acid catalyst is selected from the group consisting of Amberlyst 35, Amberlyst 15, Amberlyst 36, Amberlyst 70 and Amberlyst 131; Purolite CT-145, Lewatit S2328, Lewatit K2431, Lewatit S2568, Lewatit K2629, SK104, PK228, RCP160 and Relite RAD/F.

11. The method of claim 1 wherein the solid acid catalyst is a zeolite catalyst.

12. A method of preparing cyclic esters from 5 or 6 carbon compounds comprising, irradiating with microwaves, a liquid mixture of an inorganic acid catalyst, an organic acid and at least one of a 5 or 6 carbon compound selected from the group consisting of a sugar alcohol, a monoanhydrosugar alcohol, or a dianhydrosugar alcohol, for a time sufficient to bring the mixture to a temperature of from 120° to 200° C. for a time sufficient to from at least one of a cyclic monoester and a cyclic diester monoanhydrosugar alcohol and/or dianhydrosugar alcohol derivative of the 5 or 6 carbon compound.

13. The method of claim 12 wherein the temperature is 140° to 180° C.

14. The method of claim 12 wherein the temperature is about 160° C.

15. The method of claim 12 wherein the inorganic acid catalyst is hydrochloric acid.

16. The method of claim 12 wherein the mixture further includes an inert organic solvent.

17. The method of claim 12 wherein the starting 5 or 6 carbon compound is selected from group consisting of sorbitol, isosorbide and sorbitan.

18. The method of claim 12 wherein the starting 5 or 6 carbon compound is selected from the group consisting of arabinitol, ribitol, sorbitol, mannitol, isomannide, galactitol, iditol and xylitol.

19. The method of claim 3, wherein the starting 5 or 6 carbon compound is sorbitol.

20. The method of claim 3, wherein the starting 5 or 6 carbon compound is sorbitol, the cyclic monoester derivative is a sorbitan ester and the cyclic diester derivative is an isosorbide ester.

21. The method of claim 10 wherein the solid acid catalyst is Amberlyst 35.

22. The method of claim 1 wherein the separated 5 or 6 carbon starting compound is recycled back onto the column bed.

23. The method of claim 3 wherein the separated 5 or 6 carbon starting compound is recycled back onto the column bed.

24. The method of claim 1 wherein the organic acid is also used as the eluent for separating at least one of the cyclic monoester and diester derivative from the starting 5 or 6 carbon compound over the column bed.

25. The method of claim 3 wherein the organic acid is also used as the eluent for separating at least one of the cyclic monoester and diester derivative from the starting 5 or 6 carbon compound over the column bed.

* * * * *